United States Patent
Shah

(10) Patent No.: US 10,107,727 B2
(45) Date of Patent: *Oct. 23, 2018

(54) TISSUE PROCESSING REAGENT

(71) Applicant: Sakura Finetek U.S.A., Inc., Torrance, CA (US)

(72) Inventor: Amit D. Shah, Redondo Beach, CA (US)

(73) Assignee: Sakura Finetek U.S.A., Inc., Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/371,588

(22) Filed: Dec. 7, 2016

(65) Prior Publication Data

US 2017/0191909 A1    Jul. 6, 2017

Related U.S. Application Data

(63) Continuation-in-part of application No. 14/984,946, filed on Dec. 30, 2015, now Pat. No. 9,835,527.

(51) Int. Cl.
*G01N 1/30* (2006.01)
*G01N 1/36* (2006.01)

(52) U.S. Cl.
CPC ............... *G01N 1/36* (2013.01); *G01N 1/30* (2013.01); *G01N 2001/305* (2013.01); *G01N 2001/364* (2013.01)

(58) Field of Classification Search
CPC .......................................................... G01N 1/36
See application file for complete search history.

(56) References Cited

U.S. PATENT DOCUMENTS

| | | | |
|---|---|---|---|
| 5,422,277 | A | 6/1995 | Connelly et al. |
| 5,849,517 | A | 12/1998 | Ryan |
| 5,976,829 | A | 11/1999 | Birnboim |
| 6,017,725 | A | 1/2000 | Hoffmann et al. |
| 6,177,514 | B1 | 1/2001 | Pathak et al. |
| 6,337,189 | B1 | 1/2002 | Ryan |
| 6,458,322 | B1 | 10/2002 | Harris |
| 6,531,317 | B2 | 3/2003 | Guirguis et al. |
| 2009/0053704 | A1 | 2/2009 | Novoradovskaya et al. |
| 2014/0186882 | A1 | 7/2014 | Berberich et al. |
| 2015/0050652 | A1 | 2/2015 | Madau et al. |
| 2016/0003716 | A1 | 1/2016 | Torres et al. |

FOREIGN PATENT DOCUMENTS

WO    WO-9319209    9/1993

OTHER PUBLICATIONS

Love, et al. Cancer Research, 1954, 14:758-767.*
Andrews, "1,3,-Dioxolane, An Alternative to Formalin as a Standard for Formaldehyde", Textile Research Journal, USDA, ARS, Southern Regional Research Center, New Orleans, Louisiana 70179, U.S.A., (Dec. 1987), 705-710.
Dalpozzo, et al., "Er(OTt)3 as a Mild Cleaving Agents for Acetals and Ketals", Synthesis 2004(4): 496-498, vol. 4, (2004), 496-498.
Dalpozzo, et al., "Simple and Efficient Chemoselective Mild Deprotection of Acetals and Ketals Using Cerium(III) Triflate", American Chemical Society, J. Org. Chem., 67, (Nov. 15, 2002), 9093-9095.
Gregg, et al., "Indium(III) Triflouromethanesulfonate as an Efficient Catalyst for the Deprotection of Acetals and Ketals", American Chemical Society, J. Org. Chem. 2007, 72, (Jun. 27, 2007), 5890-5893.
Sun, et al., "Highly Efficient Chemoselective Deprotection of O,O-Acetals and O,O-Ketals Catalyzed by Molecular Iodine and Acetone", American Chemical Society, J. Org. Chem. 2004, 69, (Nov. 12, 2004), 8932-8934.
Cooper, E. A., "CXXVI. The Action of Paraldehyde Upon Proteins and Lipins", (1924), 948-950.
Sakura Finetek U.S.A., Inc., "Non final office action", U.S. Appl. No. 14/984,946, dated (Apr. 11, 2017).
Dapson, R. W., "Glyoxal fixation: how it works and why it only occasionally needs antigen retrieval", Biotechnic & Histochemistry, vol. 82, No. 3, Jan. 1, 2007, 161-166.
Sakura Finetek U.S.A., Inc., "Extended European Search Report", EP Application No. 16204884.7, dated May 17, 2017.
Sakura Finetek U.S.A., Inc., "Examination Report No. 1", AU Application No. 201677596, dated Oct. 3, 2017.
Sakura Finetek U.S.A., Inc., Canadian Examiner's Report dated Oct. 23, 2017, CA Appln No. 2,953,318.

* cited by examiner

*Primary Examiner* — Bin Shen
(74) *Attorney, Agent, or Firm* — William Thomas Babbitt; Leech Tishman Fuscaldo & Lampl, Inc.

(57) ABSTRACT

A method including placing a biological sample taken from a body into a chamber; adding a composition including an acetal solvent to the chamber; and fixating the biological sample. A method including placing a tissue from a body into a chamber; and contacting the tissue with a composition including an acetal solvent as a fixating process.

20 Claims, No Drawings

TISSUE PROCESSING REAGENT

CROSS-REFERENCE TO RELATED APPLICATION

The application is a continuation-in-part of U.S. patent application Ser. No. 14/984,946, filed Dec. 30, 2015, now issued as U.S. Pat. No. 9,835,527 and incorporated herein by reference.

FIELD

Tissue processing.

BACKGROUND

Tissues from the body taken for diagnosis of disease processes are often processed in the histology laboratory to produce thin tissue sections which can be mounted on slides and viewed under a microscope by a pathologist for analysis. These pre-analytical processes generally include, in order, gross examination fixation, dehydration, clearing, paraffin infiltration and embedding. The procedure is used for processing tissues including biopsies, larger specimens removed at surgery, or tissues from autopsy.

Gross examination generally consists of describing the macroscopic specimen and placing all or selected parts of it into a small plastic cassette which holds the tissue while it is being processed to a paraffin block. Initially, the cassettes are placed into a fixative.

Following gross examination, a tissue is fixated. A purpose of fixation is to preserve tissues permanently in as life-like a state as possible by altering structures of proteins such that degradation by autolysis does not occur. A variety of fixatives are available for use, depending on the type of tissue present and features to be demonstrated. Major groups of fixatives, classified according to mechanism of action include aldehydes, mercurials, alcohols, oxidizing agents and picrates. Formalin fixation is best carried around neutral pH, for example, in the range of 6-8. Hypoxia of tissues tends to lower the pH, so there should be buffering capacity in the fixative to prevent excessive acidity. Common buffers include phosphate, bicarbonate, malate, cacodylate, and veronal. Commercial formalin, for example, may be buffered with phosphate at a pH of 7. Penetration of tissues depends upon the diffusability of each individual fixative. One way to improve penetration of a fixative is to gross (cut) the tissue thinly (2 to 3 millimeters (mm)). Penetration into a thin tissue section will occur more rapidly than for a thick section. The volume of fixative is generally important with a 10:1 ratio or greater of fixative to tissue typically targeted. Agitation of the specimen in a fixative will often also enhance fixation.

Once the tissue has been fixed or fixated, the tissue needs to be processed into a form in which it can be made into thin sections for microscopic examination. The usual way this is done is with paraffin. Tissues embedded in paraffin, which provides a solid support matrix for the tissue, allowing it be sectioned at a thickness on the order of 2 to 20 microns. Getting fixed tissue into paraffin for sectioning is called tissue processing with the main steps in this process being dehydration, clearing, infiltration and embedding.

Tissues fixed in aqueous solutions cannot be directly infiltrated with paraffin. First, the water from the tissues must be removed by dehydration. This may be done with a series of alcohols at different concentrations (e.g., 70 percent to 95 percent to 100 percent). Alternatively, the dehydration is done with a mixture of formalin and alcohol. Other dehydrants can also be used such as acetone or mixtures of different solvents.

Following dehydration, the tissue is cleared. "Clearing" consists of removal of the dehydrant and some of the lipids with a substance that will be miscible with the embedding medium (e.g., paraffin). The most common clearing agent is xylene.

Once cleared, the tissue is infiltrated with an embedding agent such as paraffin. Finally, the tissue in a cassette or removed from its cassette is placed into molten paraffin and then the paraffin is cooled to form a solidified block embedding or encapsulating the tissue so that it can be sectioned. Alternatively, the tissue can be processed in a sectionable cassette, embedded in paraffin along with the cassette and sectioned. Once the tissue has been embedded in a solid paraffin block, the tissue can be cut into sections that can be placed on a slide. This is done with a microtome. Once sections are cut, they are floated on a warm water bath that helps remove any wrinkles. The tissue sections in paraffin are then picked up from the water bath and placed on a glass microscope slide.

DETAILED DESCRIPTION

In one embodiment, a composition including an acetal solvent is disclosed that is operable or suitable for treating a biological sample taken from a body. A biological sample such as a tissue taken from the body for diagnosis or research includes but is not limited to, a biopsy, a specimen removed at surgery and/or tissues from autopsy. Also disclosed is a method including treating a biological sample taken from a body for diagnosis with a composition including an acetal. Treating a biological sample in this regard, in one embodiment, is focused on a pre-analytical process such as fixation, clearing and/or embedding of the biological sample for subsequent examination/diagnosis.

Representative acetals suitable for a composition for treating a biological sample include methylal, ethylal, butylal, dioxolane, glycerol formal, acetaldehyde diethyl acetal and mixtures thereof. Dioxolane is one particular preferred acetal solvent. A dioxolane as described herein includes 1,3-dioxolane as well as its adducts and mixtures thereof. Such adducts include, but are not limited, to 2-methyl-1,3-dioxolane; 4-methyl-1,3-dioxolane; 2,2-dimethyl-1,3-dioxolane; 2-methyl-1,3-dioxolane; 4-methyl-2-phenyl-1,3-dioxolane (benzaldehyde propylene glycol), 1,2-dioxolane and adducts thereof. 1,3-dioxolane is one particular preferred dioxolane due to its favorable toxicity profile and commercial availability.

In one embodiment, a composition including a dioxolane is used in a process in the histology laboratory to produce microscopic slides that can be viewed under a microscope for analysis. In one embodiment, a composition including a dioxolane can be used as a dehydrating agent alone or in combination with, for example, an alcohol, acetone, xylene or glycol (separately or as a mixture). In another embodiment, the composition including a dioxolane can be used alone or in combination with an alcohol (separately or as a mixture) as a dehydration agent after a fixation process. Still further, a composition including a dioxolane can be used in an infiltration process with, for example, an additive such as paraffin to improve infiltration of the paraffin in the tissue.

As a clearing agent, a composition including a dioxolane may be used at a concentration of 100 percent (e.g., 100 percent dioxolane composition) or may be combined with another clearing agent or agents such as hydrocarbon clearing agents (e.g., xylene, hexane, mineral oil), hydrocarbon clearing agents with oxygen-based functional groups (e.g., alcohols (e.g., ethanol), acetates, ethers, acetals, etc.) or mixtures of clearing agents at a lower composition (e.g., 70 percent to 85 percent of a dioxolane with the remainder another clearing agent or agents).

The following are example uses of a composition including a dioxolane in pre-analytical processes to treat a tissue taken from a body for diagnosis.

1. The use of a dehydrating reagent such as ethanol, methanol, isopropanol, acetone etc. or combinations of such reagents to achieve dehydration of the tissues followed by use of a dioxolane as an independent reagent or as a mixture with other reagents such as ethanol, xylene, etc. for clearing. Specific examples include:

a) the use of 95 to 100 percent ethanol for dehydration followed by the use of 1,3-dioxolane for clearing;

b) the use of an ethanol-isopropyl alcohol mixture (70:30 v/v) for dehydration followed by the use of 1,3-dioxolane for clearing;

c) the use of acetone-isopropyl alcohol-ethylene glycol mixture for dehydration followed by the use of 1,3-dioxolane for clearing;

d) the use of 70 percent reagent ethanol (absolute ethanol denatured with 1 to 10 percent isopropanol and methanol) for dehydration followed by the use of 1,3-dioxolane for clearing; and e) the use of 95 to 100 percent reagent ethanol with up to 2 percent acetic acid followed by the use of 1,3-dioxolane for clearing.

2. The use of a 1,3-dioxolane-reagent ethanol mixture (e.g., 80:20, 85:15, 90:10, 95:5 v/v) for clearing.

3. The use of a dioxolane as a part of a dehydrating mixture to achieve tissue dehydration and again using the dioxolane to achieve clearing as either a standalone clearing reagent or as a part of a clearing mixture such as those listed above. Representative mixtures for dehydration include reagent ethanol (e.g., ethanol) 1,3-dioxolane mixture (70:30; 50:50 and 30:70 v/v).

4. The use of a dioxolane as an additive in paraffin wax (e.g., up to 20 percent dioxolane in paraffin) to facilitate infiltration of the wax into the tissue.

A composition including a dioxolane for a dehydrating, clearing or infiltration process may be used on conventional tissue processors for conventional processing protocols that generally are several hours long or for short protocols of lesser time (e.g., 60 minutes or less). A composition including a dioxolane can also be used in such processes on conventional tissue processors for processing protocols executed at elevated temperatures up to 70° C. reagent processing temperature. For example, a composition including a dioxolane with reagent alcohol for tissue dehydration and alone or as part of a mixture for clearing may be performed at operating temperatures with no added heat to the processing or at elevated reagent temperatures of 60° C. For infiltration processes, a composition including a dioxolane may be combined with paraffin at a temperature on the order of 65-70° C.

A composition including a dioxolane for use as a dehydrating agent, a clearing agent or an infiltration agent is also suitable with microwave assisted tissue processing for general processing protocols of about 60 minutes for regular sized tissues and shorter time periods for smaller tissues (biopsy, core, etc.)

EXAMPLES

The following represent specific examples of a use of a composition including a dioxolane in pre-analytic processing.

Example 1

Tissues were grossed and fixed in 10 percent neutral buffered formalin for 6 to 24 hours. The tissues were then placed in reagent alcohol (90-100 percent) for 30 minutes. The tissues were then placed in 1,3-dioxolane for 40 minutes, with microwave processing. Finally, the tissues were infiltrated by placement in paraffin mixed with 1,3-dioxolane (5 percent v/v) at about 65° C. for 40 minutes.

Example 2

Tissues were grossed and fixed in 10 percent neutral buffered formalin for 6 to 24 hours. The tissues were then placed in two consecutive reagent alcohol (95-100 percent) stations for 15 minutes each (or one reagent alcohol station for 30 minutes). The tissues were then placed in two consecutive 1,3-dioxolane stations for 15 minutes each. Finally, the tissues were infiltrated by placement in two consecutive paraffin (65° C.) stations for 15 minutes each.

Example 3

Tissues were grossed and fixed in 10 percent neutral buffered formalin for 6 to 24 hours. The tissues were then placed in two consecutive reagent alcohol (95-100 percent) stations for 30 minutes each (or one reagent alcohol station for 30-60 minutes). The tissues were then placed in two consecutive 1,3-dioxolane stations for 30 minutes each. Finally, the tissues were infiltrated by placement in two consecutive paraffin (65° C.) stations for 30 minutes each.

Example 4

In this example, the processing protocol of Example 2 was followed and the processing was done by microwave assist for the 1,3-dioxolane step and paraffin steps.

The above examples primarily related to the use of an acetal solvent (e.g., a dioxolane) in treating a biological sample where the treating is dehydrating, clearing or infiltrating. An acetal solvent can also be used as a fixative.

The building blocks of 1,3-dioxolane, for example, are formaldehyde and ethylene glycol or ethylene oxide. 1,3-dioxolane or formal glycol is manufactured industrially either by condensation reaction of formaldehyde with ethylene glycol in presence of Brönsted or Lewis acid catalysts or by a reaction of formaldehyde with ethylene oxide in presence of catalysts such as tin tetrachloride ($SnCl_4$), tetraethylammonium bromide ($(CH_3CH_2)_4NBr$) or toluenesulfonic acid (TsOH). Conversely, formaldehyde can be obtained by cleaving the 1,3-dioxolane molecule by hydrolysis or other methods.

Various literatures have cited ways to form aldehydes from acetals. Hydrolysis of 1,3-dioxolane reverses the condensation reaction to yield formaldehyde and ethylene glycol at relatively mild conditions. The reaction can be carried out by adding hydrochloric acid into the 1,3-dioxolane. Varying normality (N) and volume can yield varying amounts of formaldehyde in the reaction. Use of 6N HCl, for example, offers a mole of formaldehyde for each mole of 1,3-dioxolane in about four hours at room temperature.

Deprotection of acetals and ketals was shown in presence of acetone and indium(III)trifluoromethane-sulfonate (In(OTf)$_3$) as a catalyst at room temperature in a 30 minutes to eight hours duration. The reaction can be accelerated by use of microwaves at 100° C. to complete the reaction in five to 15 minutes.

A gentle Lewis acid catalyst Er(OTf)$_3$ was used for chemoselective cleavage of cyclic acetals at room temperature in wet nitromethane. Similarly, a chemoselective method for cleavage of acetals in wet nitromethane by using catalytic cetium(III)triflate at almost neutral pH offered high yields in a one to 24 hour period.

Deprotection of acyclic and cyclic acetals in excellent yields within minutes under neutral conditions in presence of a catalytic amount of iodine has also been reported.

In one embodiment, a system and process where 1,3-dioxolane is cleaved either in-situ with one or more tissues placed into it or shortly before addition of a tissue or tissues by means of catalyst, temperature, pressure, addition of water, microwave and combinations thereof is described. A portion of the 1,3-dioxolane will undergo hydrolysis to yield formaldehyde which helps with fixation of the tissue(s) while a remaining portion of the 1,3-dioxolane in the system is available to aid with processing of the tissue(s) simultaneously by dehydrating and clearing the tissue(s). The described process may be used with the tissues placed through reagent alcohol, ethanol, methanol, isopropyl alcohol, acetone or similar dehydrating agents of various concentrations for dehydration which will improve tissue clearing.

Representatively, human or animal tissues are collected and placed in a sealable container or a reaction chamber containing 1,3-dioxolane. Water and a few drops of hydrochloric acid are added to the container. The hydrolysis is carried out in relatively mild or room conditions of temperature and pressure to yield formaldehyde and ethylene glycol. The formaldehyde gas obtained in the reaction is dissolved in the water to make a formalin fixative. The process can be carried out with added buffer reagents. The reaction may also be catalyzed by use of Lewis acids, Bronsted acids and other commercial catalysts.

Fixation using an acetal such as 1,3-dioxolane may be performed on tissues that are freshly obtained, previously frozen or previously dehydrated. Formaldehyde from 1,3-dioxolane can be obtained by different methods available in literature. The hydrolysis reaction of 1,3-dioxolane can be achieved by different proton donor acid catalysts, for example, hydrochloric acid (HCl), sulfuric acid (H$_2$SO$_4$), commercially available acid based catalysts such as toluene sulfonic acid catalysts, and Lewis acids including, but not limited to, iodine, bromine, cetium (III)triflate and indium (III)trifluoromethane sulfonate. The pH of the system can be controlled by using buffer chemicals such as phosphates. Variation in concentration of the acid used in the hydrolysis reaction changes the rate of reaction and yield of formaldehyde. The ratio of 1,3-dioxolane, deionized (D.I.) water and the catalyst can be varied to vary a rate of the reaction and to vary a yield of the formaldehyde. The rate of reaction can be changed and altered by changing the reaction temperature. Higher temperature increases the rate of reaction while lower temperature reduces it. Microwave may be used to optimize rate of the reaction.

Example 5

An example of use of dioxolane as a tissue fixative is:
In 79.5 gm. 1,3-dioxolane added is 19.5 gm. D.I. water. Tissues that may be freshly obtained, previously frozen or dehydrated, are placed into the mixture of 1,3-dioxolane and water. A few drops (e.g., 2 to 4 drops) of 6N hydrochloric acid are added into the system and the reaction chamber is closed to avoid escape of formaldehyde gas. Mixing is provided to obtain a homogeneous mixture. The acid catalyzed hydrolysis reaction of the dioxolane yields ethylene glycol and formaldehyde which is expected to dissolve in the unreacted water. The freshly formed formalin reacts with the proteins in the tissues to achieve fixation while the dioxolane helps with clearing of the tissue by removing lipids.

Implementations

Implementation 1 is a method including placing a biological sample taken from a body into a chamber; adding a composition including an acetal solvent to the chamber; and fixating the biological sample.

In Implementation 2, the acetal solvent in the method of Implementation 1 includes a dioxolane.

In Implementation 3, the acetal solvent in the method of Implementation 1 includes 1,3-dioxolane.

In Implementation 4, the composition in the method of Implementation 3 includes a mixture including the dioxolane, a catalyst and water.

In Implementation 5, the catalyst in the method of Implementation 4 is an acid.

In Implementation 6, the catalyst in the method of Implementation 4 is an acid based catalyst.

In Implementation 7, the catalyst in the method of Implementation 4 is a Lewis acid.

In Implementation 8, after fixing the biological sample, the method of Implementation 5 includes dehydrating and clearing the biological sample wherein at least a part of at least one of dehydrating and clearing includes treating the biological sample with a composition including an acetal solvent.

In Implementation 9, treating the biological sample with a composition including an acetal solvent includes clearing the biological sample and, prior to clearing, the method of Implementation 8 includes dehydrating the fixated biological sample.

In Implementation 10, dehydrating of the method of Implementation 9 includes treating the fixed biological sample with a dehydrating composition including an alcohol.

In Implementation 11, the dehydrating composition of the method of Implementation 9 includes at least one of acetone and a glycol.

In Implementation 12, after fixing the biological sample, the method of Implementation 1 includes dehydrating, clearing the biological sample and infiltrating the biological sample, and infiltrating the biological sample including treating the biological sample with a composition including an acetal solvent.

In Implementation 13, the composition of the method of Implementation 11 further includes paraffin.

Implementation 14 is a method including placing a tissue taken from a body into a chamber; and contacting the tissue with a composition including an acetal solvent as a fixating process.

In Implementation 15, the biological sample of the method of any of Implementations 1-14 includes a tissue.

In Implementation 16, the acetal solvent of the method of Implementation 14 includes a dioxolane.

In Implementation 17, the composition in the method of Implementation 15 includes a mixture of the dioxolane, water and a catalyst.

In Implementation 18, the catalyst in the method of Implementation 17 is an acid.

In Implementation 19, the composition in the method of Implementation 15 includes a dehydrating process, a clearing process and an infiltration process wherein at least one of the dehydrating process, the clearing process and the infiltration process includes contacting the tissue with an acetal solvent.

In Implementation 20, the acetal solvent in the at least one of the dehydrating process, the clearing process and the infiltration process in the method of Implementation 19 includes 1,3-dioxolane.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A method comprising:
   placing a biological sample taken from a body into a chamber;
   adding a composition comprising an acetal solvent to the chamber;
   fixating the biological sample; and
   after fixating the biological sample, containing the biological sample with a paraffin.

2. The method of claim 1, wherein the acetal solvent comprises a dioxolane.

3. The method of claim 1, wherein the acetal solvent comprises 1,3-dioxolane.

4. The method of claim 3, wherein the composition comprises a mixture comprising the 1,3-dioxolane, a catalyst and water.

5. The method of claim 4, wherein the catalyst is an acid.

6. The method of claim 4, wherein the catalyst is an acid based catalyst.

7. The method of claim 4, wherein the catalyst is a Lewis acid.

8. The method of claim 1, wherein after fixating the biological sample, the method comprises dehydrating and clearing the biological sample wherein at least a part of at least one of dehydrating and clearing comprises treating the biological sample with a composition comprising an acetal solvent.

9. The method of claim 8, wherein treating the biological sample with a composition comprising an acetal solvent comprises clearing the biological sample and, prior to clearing, the method comprises dehydrating the fixated biological sample.

10. The method of claim 9, wherein dehydrating comprises treating the fixated biological sample with a dehydrating composition comprising an alcohol.

11. The method of claim 9, wherein the dehydrating composition comprises at least one of acetone and a glycol.

12. The method of claim 1, wherein after fixating the biological sample, the method comprises dehydrating, clearing the biological sample and infiltrating the biological sample, and infiltrating the biological sample comprises treating the biological sample with a composition comprising an acetal solvent.

13. The method of claim 12, wherein the composition further comprises paraffin.

14. A method comprising:
    placing a tissue taken from a body into a chamber;
    contacting the tissue with a composition comprising an acetal solvent as a fixating process; and
    after the fixating process, infiltrating the tissue with an embedding agent in an infiltration process.

15. The method of claim 14, wherein the acetal solvent comprises a dioxolane.

16. The method of claim 15, wherein the dioxolane comprises 1,3-dioxolane.

17. The method of claim 15, wherein the composition comprises a mixture of the dioxolane, water and a catalyst.

18. The method of claim 17, wherein the catalyst is an acid.

19. The method of claim 14, wherein after the fixating process, the method comprises a dehydrating process, a clearing process and then the infiltration process wherein at least one of the dehydrating process, the clearing process and the infiltration process comprises contacting the tissue with an acetal solvent.

20. The method of claim 19, wherein the acetal solvent in the at least one of the dehydrating process, the clearing process and the infiltration process comprises 1,3-dioxolane.

* * * * *